(12) United States Patent
White

(10) Patent No.: US 11,083,879 B2
(45) Date of Patent: Aug. 10, 2021

(54) VAGINAL DETOXING KIT AND METHOD

(71) Applicant: Vanessa White, Tallahassee, FL (US)

(72) Inventor: Vanessa White, Tallahassee, FL (US)

(*) Notice: Subject to any disclaimer, the term of this patent is extended or adjusted under 35 U.S.C. 154(b) by 156 days.

(21) Appl. No.: 15/472,401

(22) Filed: Mar. 29, 2017

(65) Prior Publication Data

US 2018/0280672 A1 Oct. 4, 2018

(51) Int. Cl.
*A61M 31/00* (2006.01)

(52) U.S. Cl.
CPC ... *A61M 31/002* (2013.01); *A61M 2210/1475* (2013.01)

(58) Field of Classification Search
CPC .................. A61M 31/002; A61M 2210/1475
See application file for complete search history.

(56) References Cited

U.S. PATENT DOCUMENTS

| | | | | |
|---|---|---|---|---|
| 393,546 | A * | 11/1888 | Dayan | A61F 13/2051 604/286 |
| 3,885,564 | A * | 5/1975 | Groves | A61F 13/2051 604/286 |
| 6,548,088 | B1 * | 4/2003 | Chen | A61K 36/232 424/725 |
| 2011/0152745 | A1 * | 6/2011 | Castro | A61Q 19/06 604/20 |

* cited by examiner

*Primary Examiner* — Bradley J Osinski
(74) *Attorney, Agent, or Firm* — The Rapacke Law Group, P.A.

(57) ABSTRACT

A vaginal detoxing kit comprises a vaginal insert apparatus and a hollow tube. The vaginal insert apparatus comprises a pearl shaped body and a string. Further, the pearl shaped body comprises a plurality of herbal ingredients. The string is fixedly attached to the pearl shaped body and wrapped around it. The hollow tube comprises first and second openings. A user unravels the string, inserts the string into a first opening, and draws the string through the second opening of the hollow tube. The vaginal insert apparatus is seated against the first opening of the hollow tube. The user wraps the drawn out string around a finger of the user to ensure the vaginal insert is seated firmly against the first opening. The user inserts the vaginal insert apparatus inside a vagina of the user to perform vaginal detoxing of an interior of the vagina.

15 Claims, 6 Drawing Sheets

VAGINAL DETOXING KIT AND METHOD

TECHNICAL FIELD

The present invention relates in general to vaginal detoxing and overall womb care. More particularly, the invention relates to a method of vaginal detoxing using a vaginal insert comprising herbal ingredients.

BACKGROUND

It is well known that a majority of women are affected by vaginal infections at least once during their lifetime. Generally, the interior of a vagina is home to a thriving ecosystem harboring a plurality of microorganisms. Among these microorganisms, the *Lactobacillus* species is the primary type of bacteria in a healthy vagina. The *Lactobacillus* species produce lactic acid and maintain an acidic environment, thereby inhibiting the growth of pathogenic microorganisms, for example, *Bacteroides fragilis, Escherichia coli, Gardnerella vaginalis, Neisseria gonorrhoeae, Peptostreptococcus anaerobius, P. bivia* and *Staphylococcus aureus*, etc. Hence, by the production of lactic acid, the *Lactobacillus* species drives the pH level to as low as about 3-5. Low pH levels are generally accepted as the primary determinant of the composition of the vaginal ecosystem. An unbalance in the pH levels may result in the creation of an environment conducive to excessive growth of pathogenic microorganisms. The presence of pathogenic microorganisms in large numbers lead to infections affecting the general wellness of the vaginal ecosystem. Most of these infections are caused by the excessive growth of bacteria present in the vagina, for example, *Lactobacillus* species, *Corynebacteria, Gardnerella vaginalis, Staphylococcus* species, *Peptococcus* species, aerobic and anaerobic *Streptococcus* species, and *Bacteroides* species.

Similarly, other microorganisms harbored by the vaginal ecosystem include, yeast (*Candida albicans*), protozoa (*Trichomonas vaginalis*), mycoplasma (*Mycoplasma hominis*), chlamydia (*Chlamydia trachomatis*), and viruses (e.g., Herpes simplex). Although the above-mentioned microorganisms may be present in small amounts without causing an infection, it is highly desirable that their numbers are contained to prevent an occurrence of the same. In particular, the microorganism (*Candida albicans*) causes yeast infections. Excessive growth of yeast results in symptoms such as irritation, pain during sexual intercourse, burning during urination, thick white discharge, and severe itching if untreated. The symptoms worsen before a woman's period. An apparatus and a method, which allows a woman to occasionally detox or contain excessive growth of such microorganisms within the vagina to ensure vaginal health and wellness, is required.

Hence, there is a long felt but unresolved need for an apparatus and a method, which allows a woman to occasionally detox or contain excessive growth of pathogenic microorganisms within the vagina to ensure overall vaginal health and wellness.

SUMMARY OF THE INVENTION

This summary is provided to introduce a selection of concepts in a simplified form that are further disclosed in the detailed description of the invention. This summary is not intended to identify key or essential inventive concepts of the claimed subject matter, nor is it intended for determining the scope of the claimed subject matter.

The vaginal detoxing kit and method, disclosed herein, addresses the above-mentioned need for an apparatus and a method, which allows a woman to occasionally detox or contain proliferation of pathogenic microorganisms within the vagina to ensure vaginal health and wellness. The vaginal detoxing kit comprises a vaginal insert apparatus and a hollow tube. The vaginal insert apparatus comprises a pearl shaped body and a string. Further, the pearl shaped body comprises a plurality of herbal ingredients. The string is fixedly attached to the pearl shaped body and wrapped around it. The hollow tube comprises first and second openings. In the method, disclosed herein, a user unravels the string wrapped around the substantially pearl shaped body of the vaginal insert apparatus. The user inserts the string into a first opening of the hollow tube. In an embodiment, the hollow tube is replaced by an applicator of a tampon.

The second opening of the hollow tube is smaller relative to the first opening. The user draws the string through the second opening of the hollow tube to seat the substantially pearl shaped body of the vaginal insert apparatus against the first opening of the hollow tube. The user wraps the drawn out string around a finger of the user to ensure the pearl shaped body of the vaginal insert apparatus is seated firmly against the first opening of the applicator. The user inserts the hollow tube inside a vagina of the user. The seated vaginal insert apparatus inserted into the vagina performs the vaginal detoxing of an interior of the vagina.

Other aspects, advantages, and novel features of the present invention will become apparent from the following detailed description in conjunction with the drawings.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

The specific details of the single embodiment or variety of embodiments described herein are set forth in this application. Any specific details of the embodiments are used for demonstration purposes only and no unnecessary limitations or inferences are to be understood therefrom.

Figure 1:
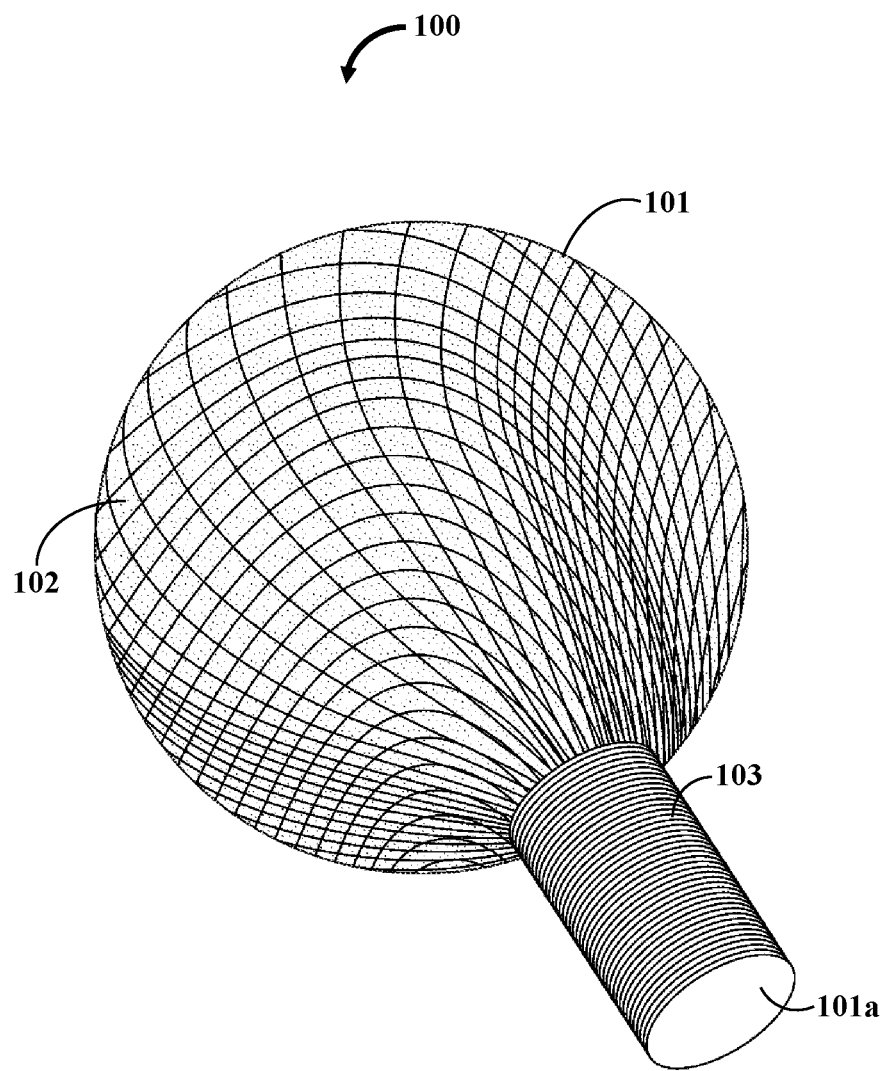
FIG. 1 exemplarily illustrates a perspective view of a vaginal insert apparatus.

FIG. 1 exemplarily illustrates a perspective view of a vaginal insert apparatus 100. The vaginal insert apparatus 100 comprises a substantially pearl shaped body 101. In an embodiment, the substantially pearl shaped body 101 comprises a tubular first end 101a. The substantially pearl shaped body 101 comprises a plurality of herbal ingredients 102. Further, a string 103 is fixedly attached to the substantially pearl shaped body 101. The string 103 is wrapped around the substantially pearl shaped body 101 as exemplarily illustrated in FIG. 1. In an embodiment, the substantially pearl shaped body 101 of the vaginal insert apparatus 100 comprises herbal ingredients 102, for example, Cnidium, Stemona, Fructus Kochiae, Motherwort, *Rhizoma, Angelica, Ligusticum Wallichii,* and Borneol. These herbal ingredients 102 are known to possess pharmacological properties for the treatment of female genitals. Furthermore, the herbal ingredients 102 have been known to exhibit strong anti-bacterial, anti-allergic, and anti-fungal properties. The herbal ingredients 102 are mixed in a proportion including 12% Cnidium, 9% Stemona, 17% Fructus Kochiae, 20% Motherwort, 15% *Rhizoma,* 13% *Angelica,* 11% *Ligusticum Wallichii,* and 3% Borneol. The vaginal insert apparatus 100 comprising the herbal ingredients 102 is inserted into the vaginal area to cleanse the vagina so that the vaginal area and uterus area function at their highest potential.

In an embodiment, women unravel the string 103 at the tubular first end 101a of the substantially pearl shaped body 101 of the vaginal insert apparatus 100. In an embodiment, an applicator of a tampon is then used to facilitate the insertion of the vaginal insert apparatus 100. In an embodiment, the vaginal insert apparatus 100 is inserted about seven centimeters into the vaginal area. Once the substantially pearl shaped body 101 of the vaginal insert apparatus 100 is inserted, the vaginal insert apparatus 100 is left untouched in the vagina for about 24 hours (1 day). After 24 hours, the vaginal insert apparatus 100 is removed and a fresh unused vaginal insert apparatus 100 is inserted with the second applicator left untouched in the vagina for about 48 hours (2 days). After 48 hours, the vaginal insert apparatus 100 is removed and the user waits for a period of three days for the "Purge" of toxins to happen. The entire process takes about 6 days to complete. Between the third and sixth days, a white discharge is noticeable normally. The discharge is released and comes down and out on its own. During this period, dryness may be experienced as well, which is normal. The user must remember to regularly hydrate oneself throughout the day. In other cases, some women experience itchiness or odor during this time. In such case, the individual is advised to take a warm bath with Epsom or Dead Sea salt, and moisturize the vaginal area with coconut oil. The toxins making their way out may temporarily cause the itchiness.

Figure 2A:
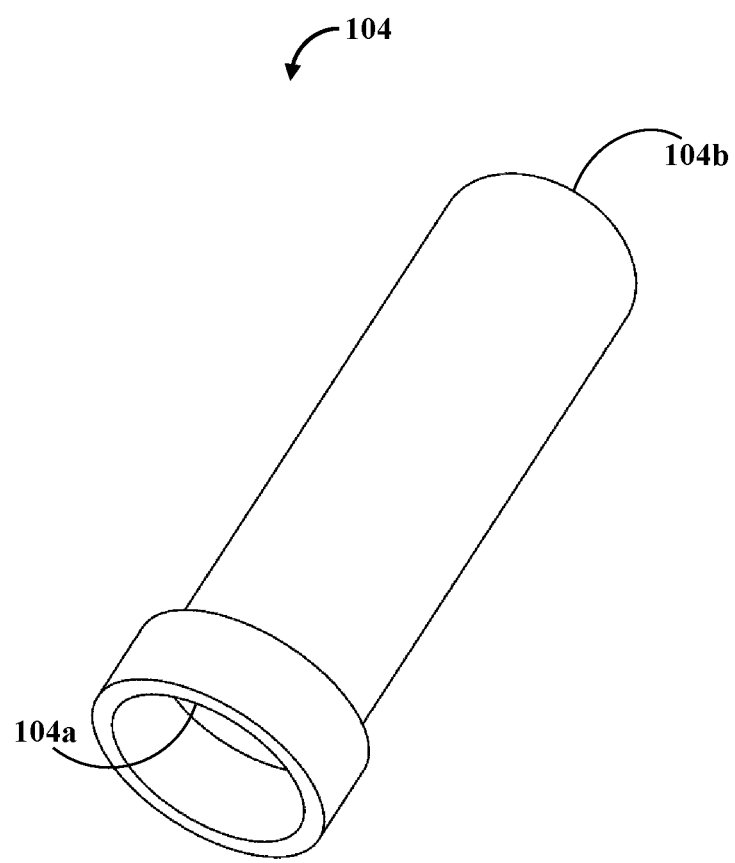
FIG. 2A exemplarily illustrates a front perspective view of a hollow tube of a vaginal detoxing kit.
Figure 2B:
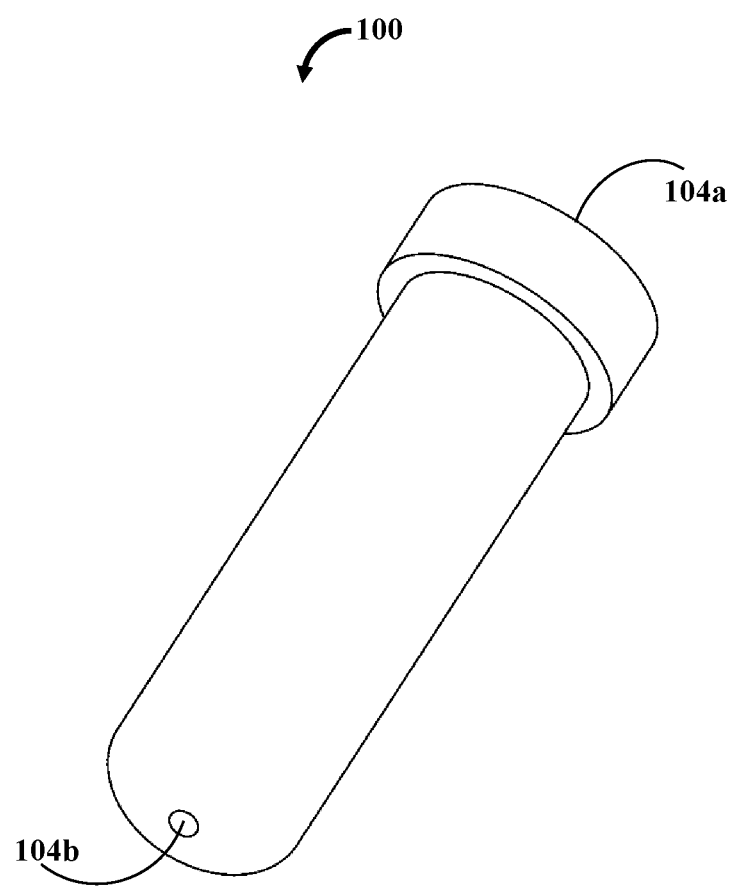
FIG. 2B exemplarily illustrates a rear perspective view of a hollow tube of a vaginal detoxing kit.

FIG. 2A exemplarily illustrates a front perspective view of a hollow tube 104 of a vaginal detoxing kit. FIG. 2B exemplarily illustrates a rear perspective view of a hollow tube 104 of a vaginal detoxing kit. In an embodiment, the hollow tube 104 comprises a first opening 104a and a second opening 104b as exemplarily illustrated in FIGS. 2A-2B. In an embodiment, the second opening 104b is smaller relative to the first opening 104a. The first opening 104a of the hollow tube 104 is large enough to accommodate the tubular first end 101a of the substantially pearl shaped body 101 of the vaginal insert apparatus 100 as exemplarily illustrated in FIG. 1. The hollow tube 104 comprises a first opening 104a and a second opening 104b. The second opening 104b is configured to receive the string 103, exemplarily illustrated in FIG. 1.

Figure 3A:
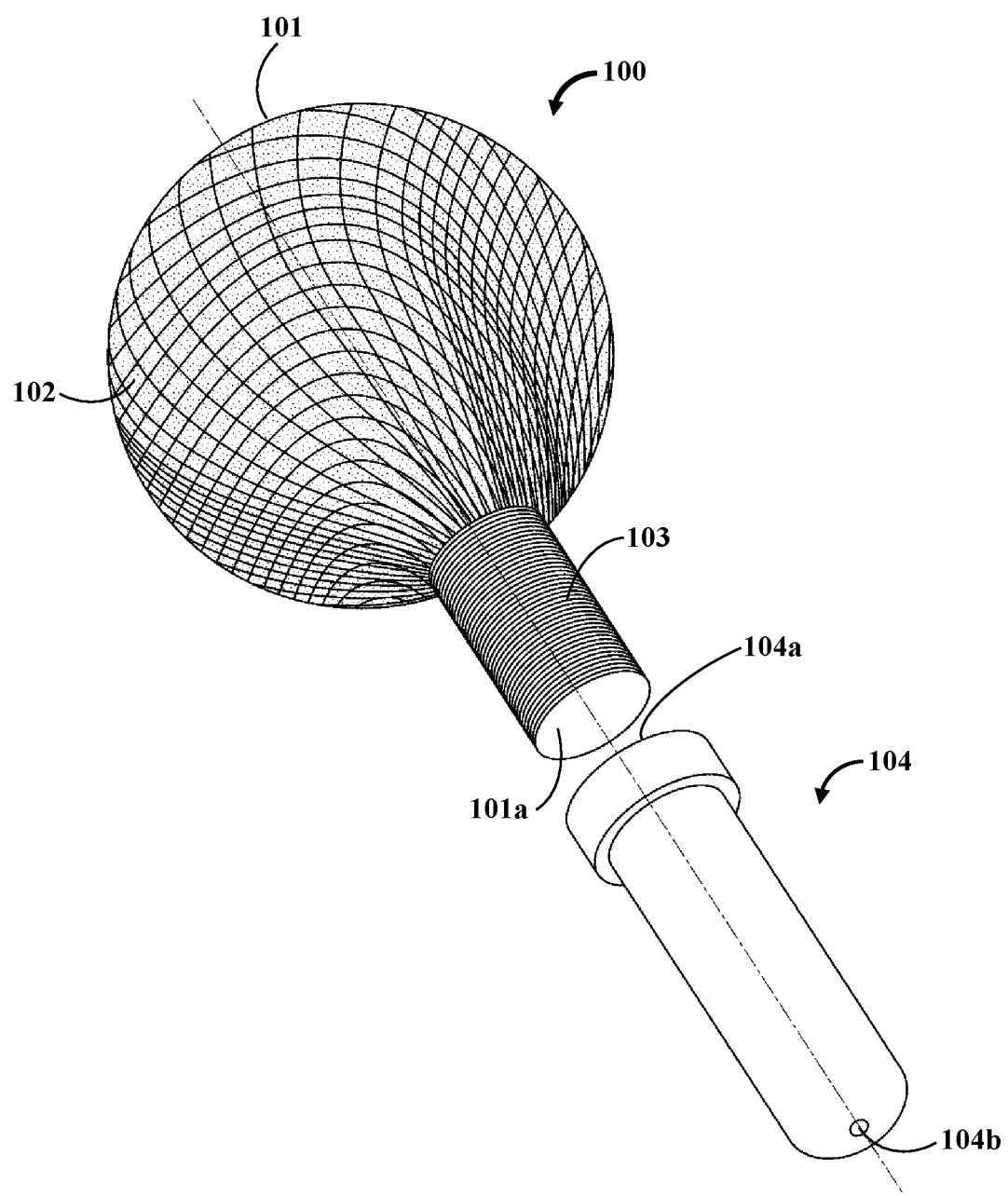
FIG. 3A exemplarily illustrates a perspective view showing components of a vaginal detoxing kit.

FIG. 3A exemplarily illustrates a perspective view showing components of a vaginal detoxing kit. The vaginal detoxing kit comprises a vaginal insert apparatus 100 and a hollow tube 104 as exemplarily illustrated in FIG. 3A. The vaginal insert apparatus 100 comprises a substantially pearl shaped body 101 and a string 103 as disclosed in the detailed description of FIG. 1. Further, the substantially pearl shaped body 101 comprises a tubular first end 101a. In an embodiment, the substantially pearl shaped body 101 is impregnated with a plurality of herbal ingredients as disclosed in the detailed description of FIG. 1. The string 103 is fixedly attached to the substantially pearl shaped body 101 and wrapped around it. The hollow tube 104 comprises a first opening 104a and a second opening 104b. The second opening 104b is provided to receive the string 103. The substantially pearl shaped body 101 is seated against the first opening 104a of the hollow tube 104 by inserting the tubular first end 101a into the first opening 104a. The substantially pearl shaped body 101 is inserted into a vagina of a user using the hollow tube for detoxing an interior of the vagina.

Figure 3B:
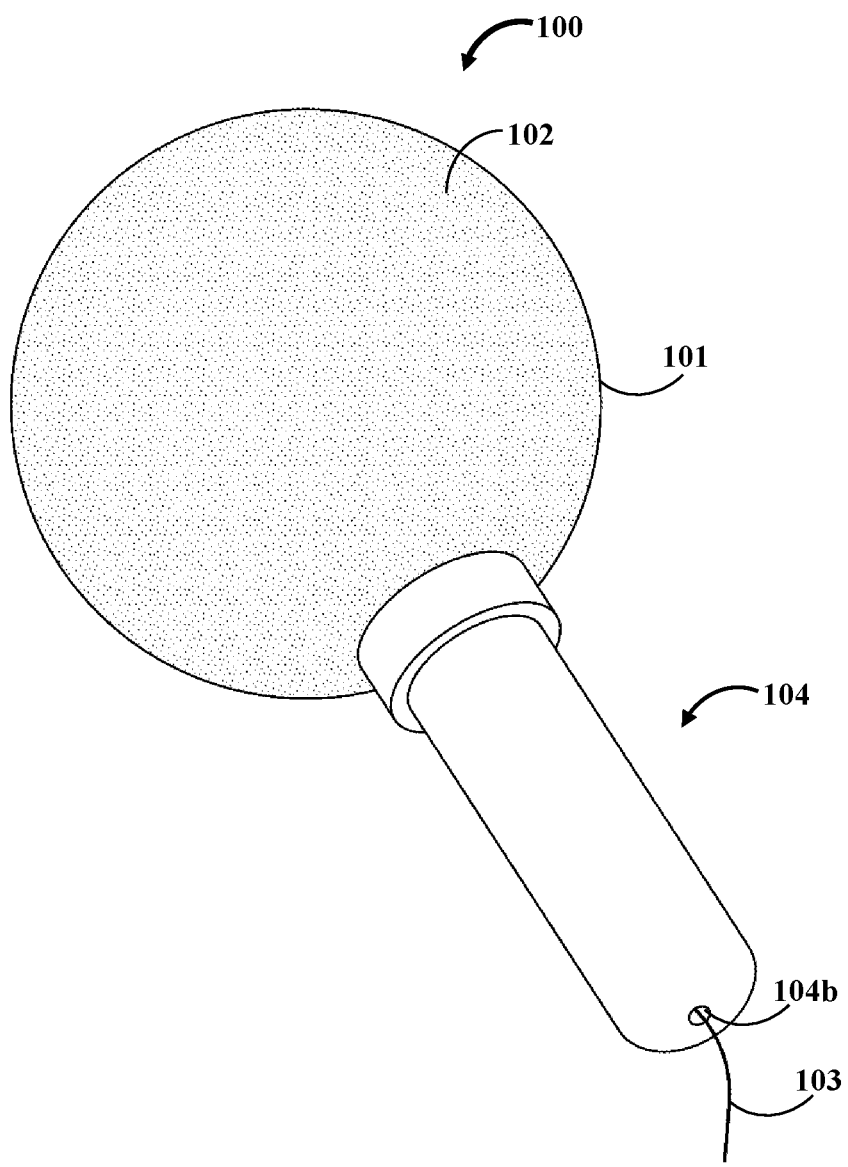
FIG. 3B exemplarily illustrates an assembled view of a vaginal detoxing kit.

FIG. 3B exemplarily illustrates an assembled view of the components of a vaginal detoxing kit. First, a user unwraps the string 103 from the substantially pearl shaped body 101 of the vaginal insert apparatus 100. The string 103 is then inserted into the first opening 104a of the hollow tube 104, exemplarily illustrated in FIGS. 2A-3A. The string 103 is then drawn through the second opening 104b. Since, the string 103 is attached to the substantially pearl shaped body 101 of the vaginal insert apparatus 100, the tubular first end 101a, exemplarily illustrated in FIG. 3A, is inserted into the first opening 104a. The substantially pearl shaped body 101 is seated against the first opening 104a of the hollow tube 104b. The user then positions the substantially pearl shaped body 101 of the vaginal insert apparatus 100 at an inclination to the entrance of the vagina. Finally, the substantially pearl shaped body 101 is inserted into a vagina of a user using the hollow tube 104 for detoxing an interior of the vagina. In an embodiment, an applicator of a tampon is used instead of the hollow tube 104.

Figure 4:
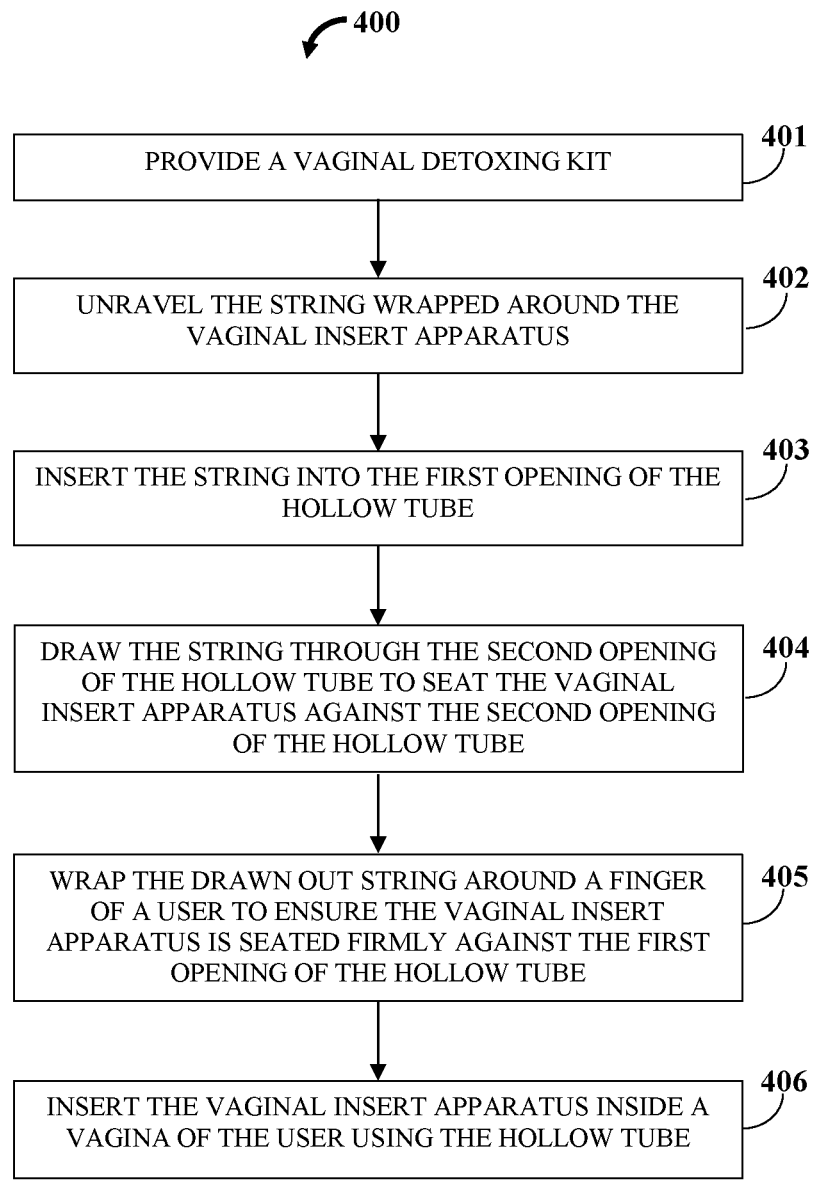
FIG. 4 exemplarily illustrates a method for vaginal detoxing.

FIG. 4 exemplarily illustrates a method 400 for vaginal detoxing. In Step 401, the method 400, disclosed herein, for vaginal detoxing comprises providing a vaginal detoxing kit as exemplarily illustrated in FIGS. 3A-3B. The vaginal detoxing kit comprises a vaginal insert apparatus 100 and a hollow tube 104. The vaginal insert apparatus 100 comprises a substantially pearl shaped body 101, a string 103, and a hollow tube 104. The substantially pearl shaped body 101 comprises herbal ingredients 102 as exemplarily illustrated in FIGS. 3A-3B. The string 103 is fixedly attached to the substantially pearl shaped body 101. Further, the string 103 is wrapped around the substantially pearl shaped body 101 as exemplarily illustrated in FIG. 1. The hollow tube 104 comprises a first opening 104a and a second opening 104b as exemplarily illustrated in FIGS. 2A-2B. In Step 402, a user unravels the string 103 wrapped around the substantially pearl shaped body 101 of the vaginal insert apparatus 100. In Step 403, the user inserts the string 103 into the first opening 104a of the hollow tube 104. In an embodiment, an applicator of a tampon is used instead of the hollow tube 104. The second opening 104b is smaller relative to the first opening 104a. In Step 404, the user draws the string 103 through the second opening 104b of the hollow tube 104 to seat the substantially pearl shaped body 101 of the vaginal insert apparatus 100 against the first opening 104a of the hollow tube 104.

In Step 405, the user wraps the drawn out string 103 around a finger of the user to ensure that the substantially pearl shaped body 101 of the vaginal insert apparatus 100 is seated firmly against the first opening 104a of the hollow tube 104. In Step 406, the user inserts the substantially pearl shaped body 101 of the vaginal insert apparatus 100 inside a vagina of the user using the hollow tube 104. The seated substantially pearl shaped body 101 of the vaginal insert apparatus 100 inserted into the vagina performs the vaginal detoxing of an interior of the vagina. Once the substantially pearl shaped body 101 is inserted via the hollow tube 104 or the applicator into the vaginal area as far as possible, the user removes her middle finger from the string 101. The string 103 should be visible and extend out of the vaginal area. The user can then remove the hollow tube 104. In an embodiment, the string 103 is worn on the outside of an underwear to make sure the user always knows where the string 103 is located. The convenience of having the hollow tube 104 used with the vaginal insert apparatus 100 allows women to have the herbal tampon inserted in different increments of time more easily so that they are more comfortable.

It will be appreciated by persons skilled in the art that the present invention is not limited to what has been particularly shown and described hereinabove. In addition, unless mention was made above to the contrary, it should be noted that all of the accompanying drawings are not to scale. A variety of modifications and variations are possible in light of the above teachings without departing from the following claims.

What is claimed is:

1. A vaginal insert apparatus, comprising:
   a substantially pearl shaped body comprising a tubular first end, wherein the substantially pearl shaped body comprises a plurality of herbal ingredients; and
   a string fixedly attached to the substantially pearl shaped body, wherein the string is wrapped around the substantially pearl shaped body;
   wherein the plurality of herbal ingredients comprises Cnidium, Stemona, Fructus kochiae, motherwort, *Rhizoma, Angelica, Ligusticum wallichii*, and borneol.

2. The vaginal insert apparatus of claim 1, wherein the plurality of herbal ingredients comprise 12% Cnidium, 9% Stemona, 17% Fructus Kochiae, 20% Motherwort, 15% *Rhizoma,* 13% *Angelica,* 11% *Ligusticum Wallichii,* and 3% Borneol.

3. The vaginal insert apparatus of claim 2, wherein the substantially pearl shaped body of the vaginal insert apparatus is capable of being inserted inside a vagina of a user.

4. The vaginal insert apparatus of claim 1, wherein the substantially pearl shaped body of the vaginal insert apparatus is capable of being inserted about seven centimeters inside a vagina of a user.

5. A vaginal detoxing kit, comprising:
   a vaginal insert apparatus, comprising:
      a substantially pearl shaped body comprising a tubular first end, wherein the substantially pearl shaped body comprises a plurality of herbal ingredients;
      a string fixedly attached to the substantially pearl shaped body, wherein the string is wrapped around the substantially pearl shaped body; and
   a hollow tube comprising a first opening and a second opening, wherein the second opening is configured to receive the string,
   wherein the substantially pearl shaped body is seated against the first opening of the hollow tube, and
   wherein the substantially pearl shaped body is capable of being inserted into a vagina of a user using the hollow tube for detoxing an interior of the vagina;
   wherein the plurality of herbal ingredients comprises Cnidium, Stemona, Fructus kochiae, motherwort, *Rhizoma, Angelica, Ligusticum wallichii*, and borneol.

6. The vaginal detoxing kit of claim 5, wherein the plurality of herbal ingredients comprises 12% Cnidium, 9% Stemona, 17% Fructus Kochiae, 20% Motherwort, 15% *Rhizoma,* 13% *Angelica,* 11% *Ligusticum Wallichii,* and 3% Borneol.

7. The vaginal detoxing kit of claim 5, wherein the second opening of the hollow tube is smaller relative to the first opening of the hollow tube.

8. The vaginal detoxing kit of claim 5, wherein the hollow tube is an applicator of a tampon.

9. A method for vaginal detoxing, the method comprising:
   providing a vaginal detoxing kit comprising:
      a vaginal insert apparatus comprising:
         a substantially pearl shaped body comprising a plurality of herbal ingredients, wherein the plurality of herbal ingredients comprises Cnidium, Stemona, Fructus kochiae, motherwort, *Rhizoma, Angelica, Ligusticum wallichii*, and borneol;
         a string fixedly attached to the substantially pearl shaped body, wherein the string is wrapped around the substantially pearl shaped body; and
      a hollow tube comprising a first opening and a second opening;
   unravelling the string wrapped around the substantially pearl shaped body of the vaginal insert;
   inserting the string into the first opening of the hollow tube;
   drawing the string through the second opening of the hollow tube to seat the substantially pearl shaped body of the vaginal insert apparatus against the first opening of the hollow tube;
   wrapping the drawn out string around a finger of a user to ensure the substantially pearl shaped body of the vaginal insert apparatus is seated firmly against the first opening of the hollow tube; and
   inserting the hollow tube with the seated substantially pearl shaped body of the vaginal insert apparatus inside a vagina of the user for a predetermined period of time.

10. The method of claim 9, wherein the plurality of herbal ingredients comprises 12% Cnidium, 9% Stemona, 17% Fructus Kochiae, 20% Motherwort, 15% *Rhizoma,* 13% *Angelica,* 11% *Ligusticum Wallichii,* and 3% Borneol.

11. The method of claim 9, wherein the second opening of the hollow tube is smaller relative to the first opening of the hollow tube.

12. The method of claim 9, wherein the hollow tube is an applicator of a tampon.

13. The method of claim 9, wherein the substantially pearl shaped body of the vaginal insert apparatus is inserted about seven centimeters inside the vagina of the user for at least 72 hours.

14. The method of claim 9, wherein the predetermined period of time is 24 hours.

15. The method of claim 9, wherein each step of the method is repeated one or more times.

* * * * *